United States Patent [19]

Jaedicke et al.

[11] 4,120,868

[45] Oct. 17, 1978

[54] CYCLIC 2-METHYL-2,4-DIALKOXY-3-BUTEN-1-AL-ACETALS, THEIR PREPARATION AND USE

[75] Inventors: Hagen Jaedicke, Ludwigshafen; Joachim Paust, Neuhofen, both of Fed. Rep. of Germany

[73] Assignee: BASF Aktiengesellschaft, Ludwigshafen, Fed. Rep. of Germany

[21] Appl. No.: 859,020

[22] Filed: Dec. 9, 1977

[30] Foreign Application Priority Data

Dec. 30, 1976 [DE] Fed. Rep. of Germany ....... 2659507

[51] Int. Cl.$^2$ ............................................. C07D 319/04
[52] U.S. Cl. ................................ 260/340.7; 260/598; 260/615 A

[58] Field of Search ..................................... 260/340.7

[56] References Cited

PUBLICATIONS

Chem. Abstracts 77:101483e.
Chem. Abstracts 83:166706y.

*Primary Examiner*—Ethel G. Love
*Attorney, Agent, or Firm*—Keil, Thompson & Shurtleff

[57] ABSTRACT

New acetals, containing a 6-membered ring, of 2-methyl-2,4-dialkoxy-3-buten-1-al, are obtained by reacting the corresponding 2-methyl-2-alkoxy-3-butyn-1-al-acetals with a mixture of the appropriate alcohol and an alkali metal alcoholate of the said alcohol at from 100° to 200° C. The acetals are intermediates for the preparation of carotinoid-based physiologically safe food dyes.

1 Claim, No Drawings

CYCLIC 2-METHYL-2,4-DIALKOXY-3-BUTEN-1-AL-ACETALS, THEIR PREPARATION AND USE

The present invention relates to new acetals, which contain a 6-membered ring, of 2-methyl-2,4-dialkoxy-3-buten-1-al, which acetals are of great importance as intermediates for carotinoid syntheses, to a process for their preparation and to their use for the preparation of 2-methyl-fumarodialdehyde-1-monoacetals.

The new compounds have the general formula I

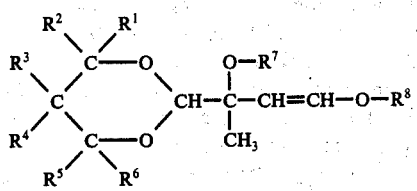

where $R^1$ to $R^6$ are H, —$CH_3$ or —$C_2H_5$, preferably H or —$CH_3$, and preferably only from 1 to 4 of the radicals $R^1$ to $R^6$ are —$CH_3$ and the remainder are H, and $R^7$ and $R^8$ are identical or different and are alkyl of 1 to 10 carbon atoms, $R^7$ preferably being —$CH_3$ or —$C_2H_5$, especially —$CH_3$, whilst $R^8$ is preferably of 4 or 5 carbon atoms.

The new 2-methyl-2,4-dialkoxy-3-buten-1-al-acetals are of great importance for the preparation of the carotinoid-based physiologically safe food dyes. Their importance resides in the fact that on the one hand they can be prepared in a simple and industrially easily realizable manner from an industrially available intermediate of an industrial synthesis of vitamin A, namely 2-hydroxy-2-methyl-3-butyn-1-al-dimethylacetal, whilst on the other hand they can be converted in an industrially easily realizable manner into the corresponding 2-methyl-fumarodialdehyde-monoacetal, which is a sought-after product. In turn, the 2-methyl-fumarodialdehyde-1-monoacetals, which have hitherto only been obtainable in accordance with German Laid-Open Application DOS 2,264,607 by a multi-stage synthesis from the less readily accessible and therefore more expensive 4-alkoxy-3-methyl-crotonaldehyde, are of great importance since by using these compounds it is possible to carry out a series of Wittig reactions to give a large number of compounds of biological and pharmacological importance. For example, retinyltriphenylphosphonium chloride, which is readily accessible and industrially available, can be elegantly converted by a Wittig olefination with 2-methyl-fumarodialdehyde-1-acetals followed by hydrolysis, into β-apo-$C_{25}$ carotinal. By comparison, the preparation of β-apo-$C_{25}$ from roughly similar structural units by conventional methods is substantially more expensive. For example, it can be prepared by linking a β-aldehyde of 19 carbon atoms with an acetal of 6 carbon atoms in accordance with the following scheme:

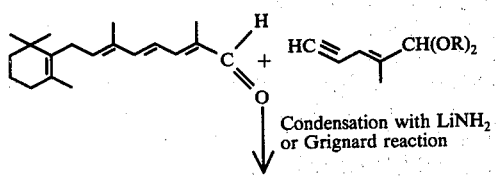

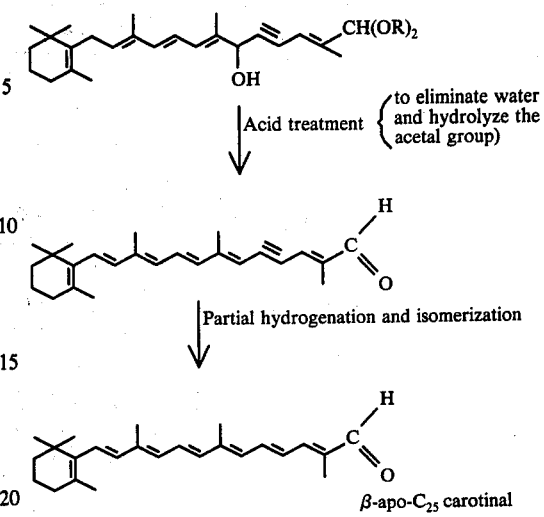

β-apo-$C_{25}$ carotinal (c.f. Helvetica Chim. Acta 42 (1959), 849, last paragraph, including the equation in the middle of page 848. As may be seen from the reaction scheme this synthesis requires, in addition to the carbon-carbon linkage and hydrolysis of the acetal groups, which our process also involves, additional synthesis steps such as partial hydrogenation and isomerization.

The present invention further relates to a process for the preparation of the cyclic 2-methyl-2,4-dialkoxy-3-buten-1-al-acetals of the general formula I as claimed in claim 1, wherein the corresponding 2-methyl-2-alkoxy-3-butyn-1-al-acetals of the formula II

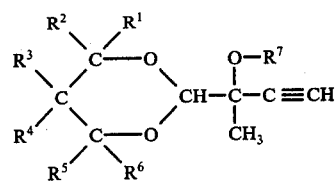

where $R^1$ to $R^6$, and $R^7$, have the above meanings, are heated with a mixture of the corresponding alcohol $R^8$-OH and an alkali metal alcoholate thereof at from 100° to 200° C.

The 2-methyl-2-alkoxy-3-butyn-1-al-acetals required as starting compounds for this process can be prepared in a simple manner, by alkylation and subsequent acid-catalyzed transacetalization with a 1,3-glycol, from 2-methyl-2-hydroxy-3-butyn-1-al-dimethylacetal, which in turn is an industrially available intermediate for an industrial synthesis of vitamin A.

Suitable alcohols of the formula $R^8$-OH are, in general, alkyl alcohols of 1 to 10, preferably of 4 or 5, carbon atoms; suitable alkali metal alcoholates are Na, K and Li alcoholates.

In general, the alcohols are employed in amounts of from 1 to 10, preferably from 3 to 5, moles per mole of starting compound; the alkali metal alcoholate is in general employed in amounts of from 0.01 to 2, preferably from 0.5 to 1, mole per mole of the acetylene compound.

The reaction only starts at temperatures above 100° C. In general, the reaction mixture is therefore heated at from about 100° to 200° C. In doing so, it is necessary to use a sealed reaction vessel when using alcohols of 1 to 3 carbon atoms. It is therefore particularly advantageous to use n-butanol or iso-butanol, which boil above 100° C. even under atmospheric pressure. The reaction mixture can be worked up in the conventional manner by distillation.

The invention further relates to the use of the new 2-methyl-2,4-dialkoxy-3-buten-1-al-acetals of the formula I for the preparation of 2-methyl-fumarodialdehyde-1-monoacetals by hydrolysis in an aqueous-organic two-phase system at a pH of from 4.5 to 6.8, preferably from 5.5 to 6.0, and at from 20° to 100° C., preferably from 35° to 45° C.

If the acetals according to the invention, of the general formula I, are to be used to prepare the corresponding 2-methyl-fumarodialdehyde-1-monoacetals, it is feasible and furthermore particularly advantageous to use the reaction solution, obtained from the reaction of the butynal-acetals of the formula II with alcohols and alcoholates, directly for the further reaction, without prior working up. However, if an alcohol of 1 to 3 carbon atoms is used as the alcohol of the formula $R^8$-OH, it is necessary to distill off the excess alcohol before further processing, since otherwise the formation of an aqueous-organic two-phase system, necessary for the hydrolysis according to the invention, is prevented.

The hydrolysis of the new 2-methyl-2,4-dialkoxy-3-buten-1-al-acetals of the formula I to give the corresponding 2-methyl-fumarodialdehyde-1-monoacetals only succeeds if very specific conditions are employed. If the reaction is not carried out in a two-phase system, but in homogeneous solution, or if the reaction is carried out in a medium having a pH of less than 4.5, or if it is carried out above 100° C., the reaction essentially gives polymers and inseparable product mixtures which are derived from the very reactive fumarodialdehydes. Even if the corresponding acetals with monohydric alcohols or with 1,2-diols are employed in place of the acetals according to the invention, of the formula I, which contain a 6-membered ring, essentially only inseparable product mixtures are obtained, and not the desired methyl-fumarodialdehyde-acetals.

To prepare an aqueous-organic two-phase system, an aqueous acid solution of the desired pH is added to the 2-methyl-2,4-dialkoxy-3-buten-1-al-acetals or to a solution of these in a solvent which is immiscible or only sparingly miscible with water, in the absence of solubilizing polar solvents, eg. acetone, alcohols of 1 to 3 carbon atoms, tetrahydrofuran or dimethylformamide. The ratio of aqueous phase to organic phase is in general from about 1:10 to 1:1 by volume.

The pH of the aqueous acid solution should be from 4.5 to 6.8, preferably from 5.5 to 6.5. Such an aqueous acid solution is obtained by dissolving an acid in water and checking the pH (for example by means of a commercial pH indicator paper) or by acidifying the aqueous phase after water has been added to the acetals of the formula I or to their solutions in solvents which are only sparingly miscible with water.

The nature of the acid used is immaterial. It is possible to use inorganic acids, organic acids or salts of strong acids with weakly basic substances. Examples of inorganic acids are hydrochloric acid, nitric acid, sulfuric acid, perchloric acid, phosphoric acid, boric acid, titanic acid, hypophosphorous acid and metaboric acid, examples of organic acids include aliphatic carboxylic acids, eg. formic acid, acetic acid, propionic acid, butyric acid, monochloroacetic acid, dichloroacetic acid, trichloroacetic acid, stearic acid, palmitic acid, acrylic acid, oxalic acid, tartaric acid and maleic acid, alicyclic carboxylic acids, eg. hexahydrobenzoic acid and naphthenic acid, aromatic carboxylic acids, eg. benzoic acid, o-, m- and p-toluic acid, phthalic acid, isophthalic acid, terephthalic acid, trimellitic acid α- and β-naphthoic acid, anisic acid, chlorobenzoic acid, nitrobenzoic acid, cyanobenzoic acid and bromobenzoic acid, aliphatic, alicyclic and aromatic sulfonic acids, eg. methane-sulfonic acid, ethanesulfonic acid, cyclohexanesulfonic acid, benzenesulfonic acid and p-toluenesulfonic acid, and phosphinic or phosphonic acids, eg. methylphosphinic acid, ethylphosphinic acid, phenylphosphinic acid, methylphosphonic acid, ethylphosphonic acid and benzylphosphonic acid, and examples of salts of a strong acid with a weakly basic substance include ammonium chloride, ammonium nitrate, ammonium sulfate, zinc chloride, ammonium p-toluenesulfonate and triethylammonium p-toluenesulfonate.

It is particularly advantageous to use an aqueous $NH_4Cl$ solution of from about 10 to 37% strength.

The 2-methyl-2,4-dialkoxy-3-buten-1-al-acetals according to the invention are of great importance for the preparation of 2-methyl-fumarodialdehyde-1-monoacetals and hence for numerous carotinoid syntheses, eg. the synthesis of β-apo-$C_{25}$ carotinal.

EXAMPLE 1

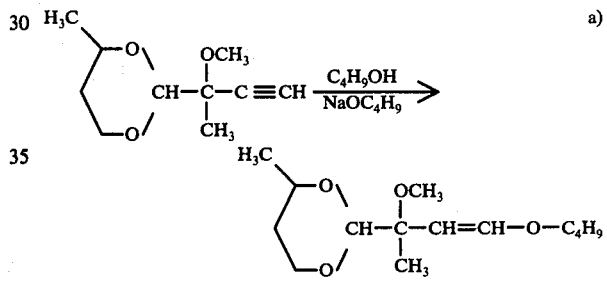

a)

36.8 g (0.2 mole) of 2-methyl-2-methoxy-3-butyn-1-al-butylene-1,3-acetal are dissolved in 74 g of n-butanol, 19.4 g (0.2 mole) of sodium n-butanolate are added to the solution and the reaction mixture is then boiled for 6 hours under reflux. When the reaction mixture has cooled, it is found by gas chromatography that 94% of the starting compound have been converted to trans-2-methyl-2-methoxy-4-n-butoxy-3-buten-1-al-butylene-1,3-acetal.

The isolated compound has a boiling point of 85° C./0.01 mm Hg.

(b) Preparation of 2-methyl-fumarodialdehyde-1-(butylene-1,3)-acetal

The reaction solution obtained according to (a) is mixed with 100 ml of water and brought to a pH of 5.5 with a 20% strength acetic acid solution. The mixture thus obtained is heated for 2 hours at 55° C., with vigorous stirring. The organic phase is then separated off and washed with dilute $NaHCO_3$ solution. The resulting mixture of butanol and the 2-methyl-fumarodialdehyde-1-(butylene-1,3)-acetal obtained can be subjected directly to a Wittig reaction.

On distillation, 29.8 g of 2-methyl-fumarodialdehyde-1-(butylene-1,3)-acetal are obtained. This corresponds to a yield of 87.6%, based on 2-methyl-2-methoxy-3-butyn-1-al-butylene-1,3-acetal employed.

EXAMPLE 2

(a)

A mixture of 39.2 g (0.2 mole) of 2-methyl-2-methoxy-3-butyn-1-al-(2',2'-dimethyl-propylene-1,3)-acetal (neopentylglycol acetal), 44.5 g of n-butyl alcohol and 17.2 g of sodium n-butanolate is heated for 7 hours at 110° C. The solution is then cooled and neutralized with 12 g of glacial acetic acid. Analysis by gas chromatography indicates a yield of 2-methyl-2-methoxy-4-n-butoxy-3-buten-1-al-neopentyl-acetal of 94% of theory, the conversion being 99%. The boiling point is 125° C./0.01 mm Hg.

(b) Preparation of 2-methyl-fumarodialdehyde-1-neopentylglycol acetal 40 ml of water are added to the solution obtained as described in (a), and the reaction mixture is brought to a pH of 6 with 1N $H_2SO_4$ and is heated for 1 hour at 60° C., whilst stirring. After the mixture has cooled, the organic phase formed is separated off and washed with dilute $NaHCO_3$ solution. Gas chromatography indicates a yield of 2-methyl-fumarodialdehyde-1-neopentylglycol-acetal of 93% of theory, based on 2-methyl-2-methoxy-3-butyn-1-al-neopentylglycol-acetal employed. Distillation gives 33.2 g (corresponding to 92% of theory) of the acetal, containing 3% of Z-constituent. The boiling point is 69° C./0.01 mm Hg.

EXAMPLE 3

Preparation of β-apo-12'-carotinal 62.8 g (0.1 mole) of retinyl-triphenylphosphonium bisulfate and 18.4 g (0.1 mole) of the 2-methyl-fumarodialdehyde-(2',2'-dimethyl-1',3'-propylene)-acetal obtained as described in Example 2 are dissolved in 200 ml of dimethylformamide at −15° C. under an inert gas and 40 g of a 30% strength solution of sodium methylate in methanol are then added dropwise. The mixture is allowed to come to room temperature, 25 ml of n-heptane and 300 ml of water are added and the phases are separated. The heptane phase is washed with twice 150 ml of 60 % strength aqueous methanol and then concentrated. The residue, 41 g of a dark red oil, is stirred for ½ hour in a mixture of 170 ml of methanol and 30 ml of 20% strength aqueous sulfuric acid at 50° C. 100 ml of water are added, the mixture is extracted with twice 100 ml of n-heptane, the heptane solution is concentrated and the treatment with aqueous methanol containing sulfuric acid is repeated. After adding 100 ml of water, the mixture is again extracted with twice 100 ml of n-heptane. After seeding at −5° C., 22.8 g of β-apo-12'-carotinal crystallize from the heptane solution in the course of about 20 hours. The mother liquor is heated for 5 hours at 105° C., concentrated to about half its volume and again kept at about −5° C., for 2 days, after seeding. Hereupon, a further 7.0 g of crystalline β-apo-12'-carotinal separate out, so that the total yield is 85%. Melting point 89°-91° C. (under nitrogen). Ultraviolet absorption: $E_1\ _{cm}^{1\%} = 2{,}190$ (petroleum ether), $\lambda_{max} = 414$ nm.

We claim:

1. A cyclic 2-methyl-2,4-dialkoxy-3-buten-1-al-acetal of the general formula I

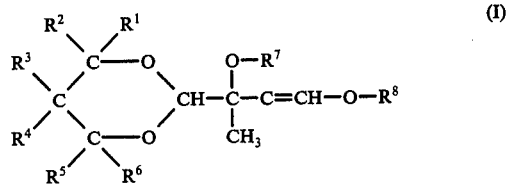

where $R^1$ to $R^6$ are H, —$CH_3$ or —$C_2H_5$ and $R^7$ and $R^8$ may be identical or different and are alkyl of 1 to 10 carbon atoms.

* * * * *